(12) United States Patent
Bidault et al.

(10) Patent No.: US 7,191,946 B2
(45) Date of Patent: Mar. 20, 2007

(54) OPTICAL IDENTIFICATION AND MARKING SYSTEM

(75) Inventors: Louis Bidault, Santenay (FR); Jacques Mugnier, Lyons (FR); Cecile Le Luyer, Villeurbanne (FR); Nicolas Bonardi, Lyons (FR)

(73) Assignee: TEB (FR)

( * ) Notice: Subject to any disclaimer, the term of this patent is extended or adjusted under 35 U.S.C. 154(b) by 278 days.

(21) Appl. No.: 10/471,134

(22) PCT Filed: Mar. 14, 2002

(86) PCT No.: PCT/FR02/00911

§ 371 (c)(1),
(2), (4) Date: Mar. 11, 2004

(87) PCT Pub. No.: WO02/075638

PCT Pub. Date: Sep. 26, 2002

(65) Prior Publication Data
US 2004/0144845 A1  Jul. 29, 2004

(30) Foreign Application Priority Data
Mar. 15, 2001 (FR) ................... 01 03554

(51) Int. Cl.
*G06K 7/10* (2006.01)
(52) U.S. Cl. .................. 235/462.05; 235/454
(58) Field of Classification Search ........... 235/462.05, 235/462.01, 462.1, 462.33
See application file for complete search history.

(56) References Cited
U.S. PATENT DOCUMENTS
4,704,519 A  11/1987 Kulikauskas 5,352,879 A * 10/1994 Milch ............... 235/462.05
5,578,809 A * 11/1996 Yamaji et al. ........ 235/462.05
6,002,139 A    12/1999 Katagiri

FOREIGN PATENT DOCUMENTS

| EP | 0 478 137 | 4/1992 |
| JP | 59 066777 | 4/1984 |
| WO | WO 87/06197 | 10/1987 |
| WO | WO 92/04192 | 3/1992 |
| WO | WO 97/50053 | 12/1997 |

OTHER PUBLICATIONS

International Search Report; PCT/FR02/00911; Jul. 18, 2002.

* cited by examiner

*Primary Examiner*—Karl D. Frech
(74) *Attorney, Agent, or Firm*—Cantor Colburn LLP

(57) ABSTRACT

The system comprises a mark (2) which is placed on an object (3) or a document, or which is constituted by the entire or part of said object, in addition to a read device (5) enabling said mark to be identified. The latter is made of transparent or semi-transparent materials having a given wavelength and capable of propagating light. The mark (2) has a surface state and a microstructure enabling optical coupling with the read device (5) comprising a monochromatic/non-monochromatic light source (11), a prism (4) onto which the light (L) is directed, and a detector (18) receiving the light reflected (R), when the prism (4) is optically coupled with the mark (2), with a frustrated reflection effect. The system can be used for the recognition of objects and documents and for the authentication of objects in order to combat fraud and counterfeiting.

24 Claims, 1 Drawing Sheet

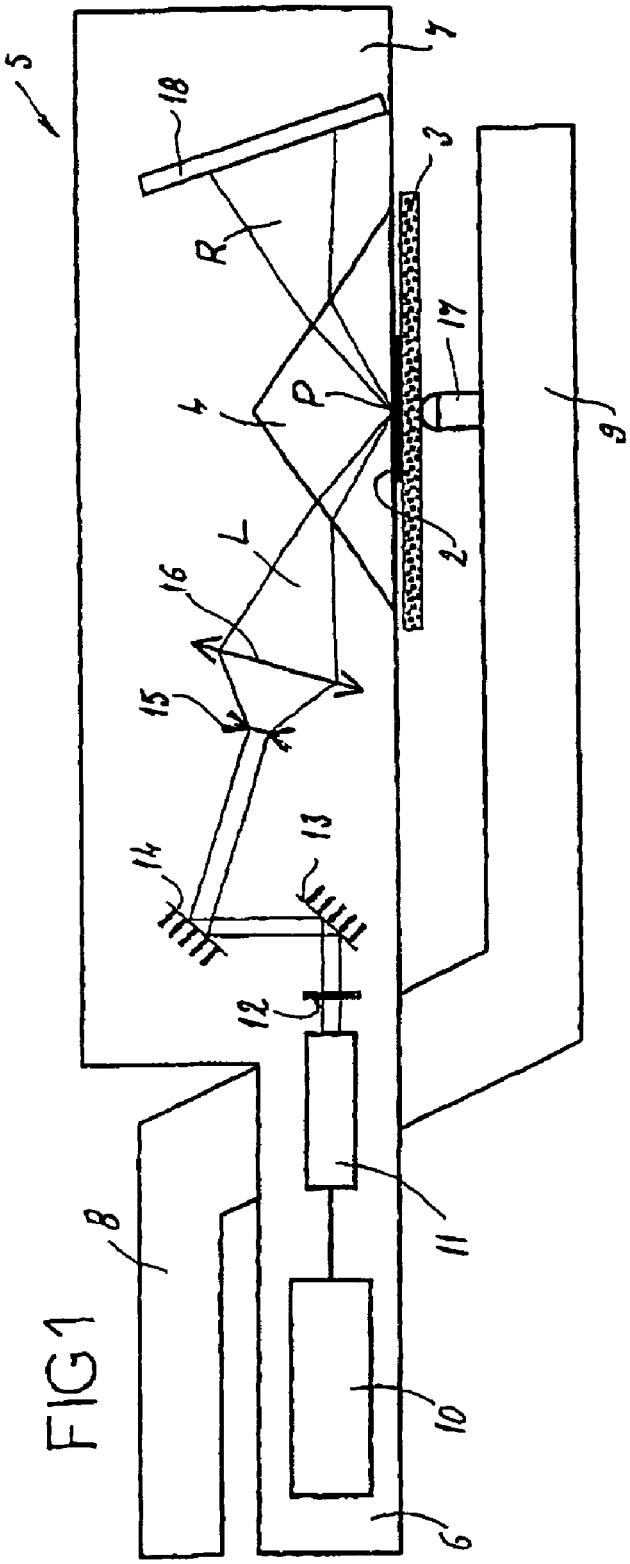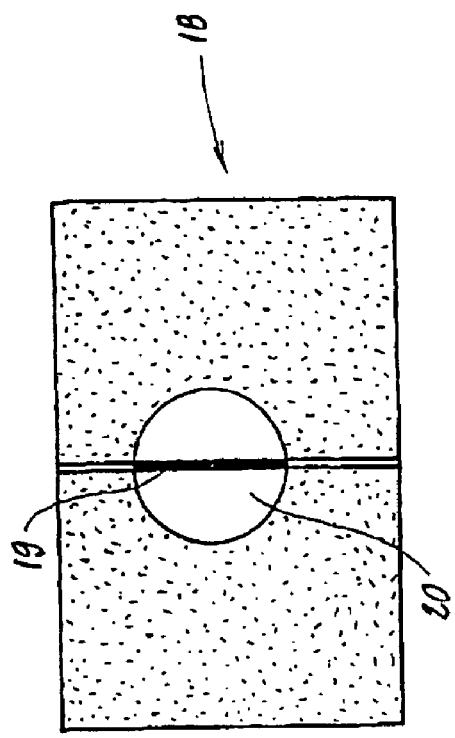

OPTICAL IDENTIFICATION AND MARKING SYSTEM

TECHNICAL FIELD OF THE INVENTION

The present invention relates to an optical marking and identification system including a mark affixed to an object or a document, or a mark formed completely or partly by the object itself, and a read device for recognizing the mark. Thus, the system allows the authentication and/or identification of objects and/or documents having a mark that is optically recognizable by a suitable read device or apparatus.

DESCRIPTION OF RELATED ART

A document or object, especially in the sense of a manufactured product, is by its nature able to be copied or falsified. For security purposes, it is desirable to protect documents and objects from fraud, imitation and counterfeiting by means of identification and recognition systems that are reliable, not easily reproducible, discreet, security-protected and difficult to falsify. For this purpose, the marking principle used is especially that consisting in affixing, to an object or document, a mark or code, having a distinctive character, and testifies to the authenticity of the object or document and is capable of being recognized using suitable means.

As regards the types of marks currently used, these are generally characters or texts that are directly readable (and easy reproducible), or coded marks that require a decryption key to be known in order to identify them, or else substances that have a distinguishable and detectable physical property (for example magnetism). The more complex the marking system and the less easy it is to immediately recognize, the less the potential counterfeiting. It is therefore necessary to find technologically complex solutions so that both reproduction and reading of the mark are made extremely difficult for the greatest number of people but remain easy to accomplish for authorized users.

The emergence of certain technologies, relying on optical properties, has provided novel solutions in this field. For example, it is known to use luminescent materials, generally called phosphors, which, when exposed to light of a given wavelength, re-emit light at another wavelength. It is thus possible to deposit, on objects or documents, marks that are invisible to the human eye but can be revealed under illumination, in the visible or infrared range, or in both, as explained in document WO 87/06197. A known variant consists in choosing the excitation and emission wavelengths in ranges that are invisible to the human eye such as, for example, the infrared range—see for example document WO 92/04192.

In such systems, the marks, before being deposited, are in a liquid form and are sometimes difficult to produce for reasons of stability or for chemical compatibility of the species present (this being the case for rare earths or luminescent molecules), or else the substances of these marks are not completely soluble and there is a risk of them obstructing the heads of the printing systems used to affix the marks to objects or documents. In addition, phosphor materials are toxic. Another major drawback of using phosphors is the deleterious influence of the substrate; when the mark is illuminated, the substrate is also excited and in turn emits light, thus appreciably disturbing the expected light signal. The latter problem means that special detectors have to be constructed, as described in document WO 97/50053 which proposes the principle of a scanning analyzer for reading marks that are fluorescent in the near-infrared range.

Finally, the principle of these above mentioned optical marks relies on the combination of a host matrix and of a substance exhibiting luminescence properties, that is to say one capable of re-emitting a signal in response to its excitation. However, any physical property associated with the chemical substance that has been introduced or can be revealed is, in principle, able to be altered or, more commonly, will degrade over time, which is difficult to accept in the case of a mark that must not be altered, even after a long time, because of the nature or the value of the objects or documents in question.

BRIEF SUMMARY OF INVENTION

The present invention aims to alleviate all these drawbacks. For this purpose, it relies on the property that certain transparent or semitransparent materials have, at a given wavelength, of propagating light. Under certain conditions, part of an incident light beam is propagated into such a material via a prism, and is thus absent from the reflected part. This behavior is well known in the technology of planar waveguides, in which the aim is in particular to guide the light into thin films.

More particularly, when a material that is transparent or semitransparent at a given wavelength is pressed against a prism, a small gap forms between the two, at the point of optical coupling. This gap may be filled with air, liquid or gas, or it may be solid. When a beam of light, especially monochromatic light, incident on the prism is focused onto the coupling point, it may happen, under certain conditions, that some of the light passes into the material by optical tunnel effect, the rest of the beam being totally reflected. Such behavior taking place at the optical coupling point is called "frustrated reflection". This particular injection of light modes arises via evanescent waves created in the gap between the prism and the guiding material, the conditions for successful propagation into this material being, among others, a refractive index of the prism higher than that of the material, a judicious angle of incidence on the prism, an incident light beam with the same polarization as the mode to be excited, a phase matching and a minimum air (or other) gap.

Analysis of the light reflected by the material, with no change in wavelength, shows the absence of the guided mode(s), this being manifested by one or more black lines on a bright background. Conventionally, the black lines are used to calculate the optical index and the thickness of thin films in planar optical waveguide technology.

A known use of this optical principle, described in document EP 0 478 137, relates to the field of biological assays and, more particularly, to demonstrating the presence of antibody-antigen binding by measuring the variation in the optical index of the solution analyzed.

However, this use remains very distant from the field of marking and identifying objects and/or documents, and no application of frustrated reflection is known, at the present time, in this field.

The present invention relies on the discovery that the black lines are an intrinsic characteristic or "signature" associated with the nature and with the morphology of the material. Such a material may therefore constitute a "mark" allowing objects or documents to be authenticated and/or identified.

Thus, the subject of the invention is essentially an optical marking and identification system, of the kind indicated in the introduction, in which the mark is composed of materials that are capable of propagating light, this mark being transparent or semitransparent at a given wavelength, and said mark having a surface finish and a microstructure that allow optical coupling with a read device that comprises at least one source of monochromatic or nonmonochromatic light, a prism onto which said light is directed and a detector that receives the reflected light, when the prism is optically coupled with the mark with a frustrated reflection effect.

Choosing such marks, used with a suitable read device, has major advantages:

In principle, the mark is passive, that is to say it does not possess physical properties that are distinguishable and able to be excited and then detected—there would be a risk of such properties deteriorating over time.

To produce such marks, it is therefore necessary to use active, generally toxic, molecules, making it conceivable for the marks to be used without exposing the public to any hazard. These marks may be formed from materials that may or may not be known for their light propagation characteristics, and preferably any material used as a waveguide. These materials may be organic, inorganic or hybrid.

The mark may have an area of the order of a few square millimeters and a thickness of at least a few tens of nanometers, these small dimensions (both in area and in thickness) making it particularly discreet.

Apart from these general features, the mark may be formed in various advantageous embodiments.

The mark may be continuous and uniform, at least over a part of its area. It may also have at least one local discontinuity such as, for example, a channel structure.

The mark may be transparent in the visible, so as not to mask the medium covered by this mark. Thus, characters printed on the medium, or drawings or other patterns on this medium, will not be masked and will remain legible through the mark, again making it very discrete by these means.

According to another embodiment, the mark is covered with a protective and/or decoy-acting layer, that can be removed before reading; this may be a soluble layer, a plasticized layer or any other type of protective layer.

The mark may contain a material such as a dye or phosphor, or another agent able to modify the appearance thereof and/or to be involved in the detection process; this means makes it possible to locate the mark, but also to divert possible counterfeiters from the true property to be analyzed.

The mark is also locally modifiable, reversibly or irreversibly, especially by chemical, physical or mechanical means, as regards the optical properties of the material of this mark, and more particularly the optical index.

According to one embodiment, the mark is made in the form of one or more layers, particularly in the form of a thin layer, deposited on or fixed to the object or document to be marked. The mark is thus in the form of a patch, possibly transparent, with an area of the order of a few square millimeters and with a thickness of at least a few tens of nanometers (as already indicated above).

Before deposition, the material of the mark may be in liquid form, which allows it to be deposited, for example, by spraying or by an "inkjet" technique or by any other technique for depositing thin films or layers. The film thus deposited may be subjected to a heat or other treatment with a view to giving it good mechanical and structural properties such as, for example, stability over time, hardness and abrasion resistance.

Since the information contained in the deposited layer is independent of the medium or substrate, it is conceivable to deposit the mark on any type of medium or substrate, such as on paper, metals, plastics, semiconductors, or functionalized substrates such as integrated circuits, thereby providing the optical marking and identification system according to the invention with a very wide field of application. The mark may be deposited directly on the substrate, or else separately and then affixed, for example, by adhesive bonding, to the substrate. Another method of producing it consists in making the mark in the form of a self-supporting film.

According to one particular embodiment, the mark is deposited on a preparatory underlayer, especially an optical substrate, the refractive index of which is generally lower than that of the constituent material of the mark. This underlayer or optical substrate, deposited on the medium before the layer actually containing the information is deposited, may be useful especially when the medium is not transparent at the working wavelength.

According to another embodiment, the mark is formed by a multilayer (a stack of successive layers). Such a multilayer gives rise to a larger number of propagated modes, and therefore of black lines, thereby making it possible to have a greater variety of combinations, and therefore of marks. In this case, the mark may be initially formed from several layers, but it is also possible to add one or more layers to a pre-existing mark, in order to modify it if so required. The latter possibility is particularly beneficial for the purpose of traceability, as evidence of an object or product having passed along a production line, or as evidence of the object being sold, or for marking any step in a process.

According to another embodiment, the mark has some bulk, that is to say it has a thickness typically of between a few tens and a few hundred micrometers, but without any upper thickness limit being imposed. This is the case, in particular, for a mark formed by all or part of the object or document itself, if this object or document is made, completely or partly, of a material whose intrinsic properties allow light propagation. In this case, the projection of the reflected light onto the detector shows a dark region, corresponding to the cutoff frequency, i.e. to the continuum of modes guided by the material, and a light region. The angular position of the boundary between the two regions is characteristic of the optical index of the material, but also of the read device (prism, working wavelength, position of the detector). A nonguiding colored layer may be deposited on the material of the object or document, so as to deceive would-be counterfeiters.

According to one embodiment of the invention, the mark is capable of being identically reproduced on a large number of objects or documents. In other words, series of identical marks are affixed to objects and/or documents, which makes mass-marking possible, on the same series of objects and/or documents.

According to another embodiment of the invention, each mark is unique and assigned to one object or document that is thus characterized thereby. In this case it is possible to establish a database in which the characteristics of the marks, all unique, are stored; the object or document is identified or authenticated by comparing what the detector reads with the data stored in memory.

Another aspect of the invention relates to the device for reading the mark. According to a preferred embodiment, this read device comprises, in combination:

at least one light source delivering a beam of polarized or unpolarized light;

a prism, having a refractive index greater than that of the mark, optically coupling with the mark at a given point;

optical means for directing and/or conveying the beam of light onto the prism at the optical coupling point; and a detector placed so as to receive the reflected light after coupling with the mark.

The or each light source may be a monochromatic source, such as a laser or laser diode, that delivers the monochromatic or quasi-monochromatic light beam directly, such as a light-emitting diode, of chosen wavelength. The or each light source may also be a polychromatic source, optionally coupled to one or more optical filters of suitable passband.

The incident light beam must be directed onto the optical coupling point in order to allow the guided modes to pass into the mark. For this purpose the optical means, that direct the incident beam onto the prism, may comprise lenses, at least one of which is a convergent lens placed in front of the prism, and possibly a system of mirrors. The convergent lens, placed in front of the prism, makes it possible to have several simultaneous angles of incidence, and therefore several modes propagated simultaneously, i.e. several black lines on the detector.

In the simplest case, the system comprises a single monochromatic light source, but it may also be designed for several monochromatic light sources operating simultaneously in the same read device and with the same detector, thereby making it possible to form a larger number of black lines on this detector, and therefore a larger number of possible codings. Within the same context, a single monochromatic light source may be polarized in TE or TM mode by the simple action of a polarizer, thereby affording the possibility of doubling the information contained in the mark.

The detection of the signal delivered by the mark may be simple, i.e. purely visible (on a screen). This detection may also include electronic means for the acquisition, processing and storage of the signal received, to which means the detector that receives the light reflected by the prism is coupled. In the latter case, the detection devices that can be used are, for example, those known for reading bar codes, or photodetectors, or else a CCD camera.

In a simplified version, the reading takes place by analyzing the light intensity received. Any reduction in intensity is interpreted as a success, that is to say that the object or document has been correctly identified or authenticated by its mark being recognized, and the system then delivers a success message.

In a more complex version, the electronic means may analyze, on the basis of the reflected light after contact with the mark, one or more of the following parameters: the index of the mark, the thickness of the mark, the number and/or spacing and/or positions and/or width of the black or white lines on the detector, the position of the cutoff frequency, the mean light intensity received by the detector, the mean index and/or the mean thickness in the case of a multilayer mark, and the additional lines when phosphors are present in the mark. In the case of a polarized light beam, said electronic means are also designed to analyze each light mode according to its polarization.

Furthermore, the nature of the light source and/or the nature and/or the geometrical shape of the prism and/or of other features of the read device are used as security parameters of the system. In other words, a mark may be read, and consequently considered as being valid, only by a read device having the precise technical characteristics, thereby constituting an additional security parameter for the system according to the invention.

When the read device is being used, and so that reading is possible, the prism has to be in optical contact with the mark. The practical embodiments of the read device must satisfy this requirement.

According to a first practical embodiment, the device for reading the mark is a portable device in the form of pincers, one jaw of which includes the prism and the other jaw of which includes, opposite the prism, an element that allows optical coupling between the mark to be analyzed, said mark being introduced between the two jaws of the pincers, and said prism. The mark to be analyzed is thus gripped between the jaws of the pincers.

According to another practical embodiment, the device for reading the mark is a portable device of elongate shape, one end of which is provided with the prism and is designed to be applied against the mark to be analyzed. In another kind of specific embodiment, the device for reading the mark is a stationary or semi-movable apparatus into which the mark to be analyzed is introduced, it being possible for means to be provided in this apparatus for automatic optical coupling between the prism and this mark. When the object or document is introduced into the apparatus, an automatic system guides it so as to bring its mark to the optical coupling point, where the coupling may also be automated, for example by means of a pneumatic device.

BRIEF DESCRIPTION OF THE DRAWINGS

The invention will in any case be more clearly understood with the aid of the following description, with reference to the appended schematic drawings that show, by way of example, one embodiment of this optical marking and identification system:

FIG. 1 shows a mark deposited on a medium and an associated portable read device; and FIG. 2 illustrates the image obtained on the detector of the read device.

DETAILED DESCRIPTION OF THE INVENTION

Referring to FIG. 1, a thin film 2 of material transparent or semitransparent at the working wavelength, with an optical index $n_f$, constituting in this case the mark, is deposited on a medium 3 that corresponds to the object or document marked. The medium 3, with an optical index $n_m$ of less than the index $n_f$ of the film 2, acts as optical substrate. A combination formed by the mark 2 and its medium 3 is designed here to be brought manually into optical contact with a prism 4, which belongs to an optical read device denoted overall by the reference number 5, the optical index $n_p$ of the prism 4 being higher than the index $n_f$ of the film 2. We therefore have the relationship:

$$n_p > n_f > n_m.$$

The read device 5 shown is a portable device, made in the form of pincers having two mutually articulated branches, i.e. a "fixed" first branch, forming a handle 6 and having a jaw 7, and a "moving" second branch, forming a complementary handle 8 and having another jaw 9, located opposite the first jaw 7.

The components of the read device 5 that are housed in the "fixed" branch of the pincers comprise a power supply 10, ensuring that the device is self-sufficient, which supplies a light source 11 delivering a monochromatic light beam of defined wavelength, intensity and polarity. The source 11 may be formed by a laser or laser diode, or a lamp with a filter, combined with a polarizer 12.

Since the prism 4 is housed in the jaw 7 of the "fixed" branch, opposite the jaw 9 of the "moving" branch of the pincers, the beam emitted by the light source 11 is directed toward the prism 4 via an optical system comprising, in succession, a first mirror 13, a second mirror 14, a divergent lens 15 and a convergent lens 16. The divergent lens 15 acts as a beam expander. The convergent lens 16, which is placed immediately in front of the prism 4, is chosen so as to have, as characteristics, a large diameter and a short focal length, thereby making it possible to obtain several angles of incidence, and therefore to inject several light modes simultaneously inside the mark 2. The incident light beam L thus directed onto the prism 4 is focused onto an optical coupling point P.

The jaw 9 of the "moving" branch of the pincers carries, opposite the first jaw 7 and more particularly facing the coupling point P, a coupling finger 17 designed to be applied beneath the medium 3 when the mark 2 is introduced between the two jaws 7 and 9.

The read device 5 also includes, near the end of the jaw 7, a detector 18 made in the form of a screen, visible from the outside (see also FIG. 2). The detector 18 is placed so as to be reached by the reflected beam R leaving the prism 4.

To use the read device 5, the assembly formed by the mark 2 and its medium 3 is engaged between the two jaws 7 and 9 of the pincers and, by manually gripping the handles 6 and 9 together, which action presses the coupling finger 17 against the medium 3, the desired optical coupling between the prism 4 and the mark 2 is obtained, with the optimum air gap at the prism 4/mark 2 interface. With the light source 11 activated, the modes can be injected from the prism 4 into the mark 2 according to the principle of frustrated reflection. The part reflected off the mark 2 leaves the prism 4 and strikes the detector 18. The absence of a natural mode in the reflected beam R is manifested, on the detector 18, by a contrast variation, such as a black line 19 on a light background 20 (see FIG. 2), or vice versa. This variation, that can be analyzed in terms of width, intensity and other characteristics associated with the mark 2, constitutes the indicator of successful analysis of the mark 2.

The system described above is particularly intended for the recognition of objects and documents, and also their authentication with a view to protecting them from fraud and counterfeiting.

It should be noted that the mirrors, needed to guide the light in the example illustrated, because of the configuration of the read device and the little space available inside it, may be omitted in the case of an apparatus in which the light source can be in alignment with the lenses. It would also be possible to replace the mirrors with optical fibers, in order to convey the light to the convergent lens placed in front of the prism. Within the same context, the detector may be of any suitable type. The read device may also be tailored to particular objects.

The invention claimed is:

1. An optical marking and identification system, comprising:
    a mark affixed to an object, or a mark formed by all or part of the object; and
    a read device for recognizing said mark;
    wherein the mark comprises materials that are capable of propagating light, the mark being transparent or semi-transparent at a given wavelength, and said mark having a surface finish and a microstructure that allow optical coupling with the read device; and
    wherein the read device comprises at least one source of monochromatic or nonmonochromatic light, a prism onto which said light is directed, and a detector that receives the light reflected when the prism is optically coupled with the mark with a frustrated reflection effect;
    wherein the device for reading the mark further comprises:
        at least one light source delivering a beam of polarized or unpolarized light;
        the prism, having a refractive index greater than that of the mark, optically coupling with the mark at a given point;
        optical means for directing and/or conveying the beam of light onto the prism at the optical coupling point; and
        a detector disposed so as to receive the reflected light after coupling with the mark.

2. The system as claimed in claim 1, wherein the mark is continuous and uniform, at least over part of an area of the mark.

3. The system as claimed in claim 1, wherein the mark has at least one local discontinuity.

4. The system as claimed in claim 1, wherein the mark is transparent in the visible, so as not to mask a medium for the mark.

5. The system as claimed in claim 1, wherein the mark comprises a material such as a dye or a phosphor, or another agent able to modify an appearance thereof and/or to be involved in a detection process of the mark.

6. The system as claimed in claim 1, wherein the mark is locally modifiable, reversibly or irreversibly, by chemical, physical or mechanical means, as regards optical properties of the material of the mark.

7. The system as claimed in claim 1, wherein the mark is covered with a protective and/or decoy-acting layer, that can be removed before reading.

8. The system as claimed in claim 1, wherein the mark is formed by a multilayer.

9. The system as claimed in claim 1, wherein the mark is made in the form of a thin layer deposited on or fixed to the object to be marked.

10. The system as claimed in claim 1, wherein the mark is made in the form of a self-supporting film.

11. The system as claimed in claim 1, wherein the mark is deposited on a preparatory underlayer.

12. The system as claimed in claim 1, wherein the mark has some bulk and may be formed by the object to be marked itself.

13. The system as claimed in claim 1, wherein the mark is identically reproducible on a large number of objects or documents.

14. The system as claimed in claim 1, wherein the mark is unique and thus characterizes only a single object.

15. The system as claimed in claim 1, wherein the light source is a monochromatic source delivering the beam of monochromatic light directly.

16. The system as claimed in claim 1, wherein the light source is a quasimonochromatic or polychromatic source.

17. The system as claimed in claim 1, wherein the optical means that direct the incident beam onto the prism comprise lenses, at least one of which is a convergent lens placed in front of the prism, and a system of mirrors.

18. The system as claimed in claim 1, wherein the detector that receives the light reflected by the prism is coupled to electronic means for the acquisition, processing and storage of a signal received.

19. The system as claimed in claim 18, wherein said electronic means are designed to analyze, on a basis of the reflected light after contact with the mark, at least one of: an index of the mark, a thickness of the mark, a number of black lines or white lines on the detector, a spacing of the black lines or the white lines an the detector, positions of the black lines or the white lines on the detector, a width of the black or the white lines on the detector, a position of a cutoff frequency, a mean light intensity received by the detector, a mean index where the mark is the multilayer mark, a mean thickness where the mark where the mark is a multilayer mark is a multilayer mark, and additional lines when phosphors are present in the mark.

20. The system as claimed in claim 19, wherein the light is a beam of polarized light and said electronic means are designed to analyze each light mode according to its polarization.

21. The system as claimed in claim 1, wherein a nature of at least one of the light source, a geometrical shape of the prism, and of other features of the read device are used as security parameters of the system.

22. The system as claimed in claim 1, wherein the device for reading the mark is a portable device in a form of pincers, comprising a first jaw which includes the prism and a second jaw which includes, opposite the prism, an element that allows optical coupling between the mark to be analyzed, said mark being introduced between the two jaws of the pincers, and said prism.

23. The system as claimed in claim 1, wherein the device for reading the mark is a portable device of elongate shape, one end of which is provided with the prism and is designed to be applied against the mark to be analyzed.

24. The system as claimed in claim 1, wherein the device for reading the mark is a stationary or semi-movable apparatus into which the mark to be analyzed is introduced, the apparatus including means for automatic optical coupling between the prism and the mark.

* * * * *